US012562280B2

(12) United States Patent
Arkoff et al.

(10) Patent No.: US 12,562,280 B2
(45) Date of Patent: Feb. 24, 2026

(54) MULTILINGUAL HEALTHCARE SYSTEM WITH PERSONALIZED MEDICAL ASSISTANT, DECISION SUPPORT, AND CLOSED-LOOP DEVICE CONTROL

(71) Applicant: OneSource Solutions International, Inc., Sudbury, MA (US)

(72) Inventors: Harold Arkoff, Sudbury, MA (US); Vedran Jukic, Trieste (IT)

(73) Assignee: OneSource Solutions International, Inc., Sudbury, MA (US)

( * ) Notice: Subject to any disclaimer, the term of this patent is extended or adjusted under 35 U.S.C. 154(b) by 0 days.

(21) Appl. No.: 19/270,319

(22) Filed: Jul. 15, 2025

(65) Prior Publication Data

US 2026/0024661 A1     Jan. 22, 2026

Related U.S. Application Data

(60) Provisional application No. 63/672,848, filed on Jul. 18, 2024.

(51) Int. Cl.
| | |
|---|---|
| *G16H 50/20* | (2018.01) |
| *G16H 10/60* | (2018.01) |
| *G16H 20/00* | (2018.01) |
| *G16H 40/67* | (2018.01) |
| *G16H 80/00* | (2018.01) |

(52) U.S. Cl.
CPC ............. *G16H 50/20* (2018.01); *G16H 10/60* (2018.01); *G16H 20/00* (2018.01); *G16H 40/67* (2018.01); *G16H 80/00* (2018.01)

(58) Field of Classification Search
CPC ............................... G16H 50/20; G16H 40/67
See application file for complete search history.

(56) References Cited

U.S. PATENT DOCUMENTS

| | | | | |
|---|---|---|---|---|
| 7,447,643 | B1 * | 11/2008 | Olson ...................... | G16Z 99/00 |
| | | | | 706/46 |
| 10,446,273 | B1 * | 10/2019 | McNair .................. | G16H 15/00 |

(Continued)

*Primary Examiner* — Van C Mang
(74) *Attorney, Agent, or Firm* — IP Consulting Group; Michael Razavi; Alfred F. Hoyte, Jr.

(57) ABSTRACT

The present invention provides a multilingual, AI-powered healthcare system integrating a personalized medical assistant, real-time clinical decision support, and closed-loop device control. The system ingests multimodal patient-generated and institutional data, applies advanced language-model-driven reasoning for clinical insights and triage, and supports regulated, auditable actuation of medical devices. Key features include multilingual overlays, role- and jurisdiction-specific visualization, co-signature enforcement, audit traceability, and seamless integration with healthcare infrastructure. A "Multilingual Overlay" is a dynamically generated display layer that the system composites in real-time from clinical text, icons, and color-coded indicators, automatically adapting its language, reading direction, terminology, visual density, and role-based data visibility to the preferences, locale, and device form-factor of each authenticated viewer. The architecture supports provider- and patient-facing use cases, agentic AI for autonomous yet regulated decision-making, and robust safety and compliance features.

22 Claims, 7 Drawing Sheets

(56)         References Cited

U.S. PATENT DOCUMENTS

| | | | | |
|---|---|---|---|---|
| 11,494,669 | B2 * | 11/2022 | Hazard | G06N 20/00 |
| 11,868,613 | B1 * | 1/2024 | Raffy | G06N 20/10 |
| 11,894,127 | B1 * | 2/2024 | McNair | G06Q 10/0639 |
| 2003/0110059 | A1 * | 6/2003 | Janas, III | G16H 40/20 |
| | | | | 705/2 |
| 2009/0030731 | A1 * | 1/2009 | Reiner | G06Q 10/00 |
| | | | | 434/323 |
| 2019/0311220 | A1 * | 10/2019 | Hazard | G06F 18/2148 |
| 2019/0333636 | A1 * | 10/2019 | Bennett | G16H 50/00 |
| 2023/0104655 | A1 * | 4/2023 | Amarasingham | G16H 15/00 |
| | | | | 705/2 |
| 2023/0153539 | A1 * | 5/2023 | Uhl | G06N 3/0895 |
| | | | | 705/2 |
| 2023/0170092 | A1 * | 6/2023 | Moon | G16H 10/60 |
| | | | | 705/2 |
| 2023/0317261 | A1 * | 10/2023 | Vanggaard | G16H 70/20 |
| | | | | 705/2 |
| 2024/0257928 | A1 * | 8/2024 | Harnach | G16H 50/20 |
| 2025/0006376 | A1 * | 1/2025 | Soori-Arachi | G06V 10/82 |
| 2025/0087342 | A1 * | 3/2025 | Khosla | G16H 40/20 |
| 2025/0259082 | A1 * | 8/2025 | Crabtree | G06N 3/047 |
| 2025/0267173 | A1 * | 8/2025 | Cline | H04L 63/20 |

* cited by examiner

1

MULTILINGUAL HEALTHCARE SYSTEM WITH PERSONALIZED MEDICAL ASSISTANT, DECISION SUPPORT, AND CLOSED-LOOP DEVICE CONTROL

CROSS-REFERENCE TO RELATED APPLICATIONS

This application claims priority under 35 U.S.C. § 119(e) to U.S. Provisional Application No. 63/672,848, filed on 18 Jul. 2024 and entitled Multilingual AI-Powered Healthcare System with Personalized Medical Assistant, Decision Support, and Closed-Loop Device Control, which is incorporated by reference in its entirety.

This application is also related to—and incorporates by reference—the following OSSI patents and utility applications:

U.S. Pat. No. 11,532,393—"Comprehensive Healthcare Data Management System."

U.S. Pat. No. 11,693,990—"Medical Data Governance."

U.S. Pat. No. 12,001,464—"System and Method for Medical Data Governance Using Large Language Models."

U.S. Pat. No. 12,002,579—"Wearable Medical-Device Data Connectivity System and Method."

U.S. Pat. No. 12,327,634—"Operating-Room Management System with Mobile Application."

U.S. application Ser. No. 18/520,430—Medical Data Governance System (Wearable/Recapture CIP).

U.S. application Ser. No. 19/221,392—Policy-Constrained Symbolic Rendering of AI Outputs

FIELD OF THE INVENTION

The disclosure relates to computer-implemented medical-information processing systems and, more particularly, to multilingual artificial-intelligence (AI) platforms that ingest heterogeneous clinical-data streams, generate context-aware decision support, and safely actuate connected medical devices in compliance with regulatory requirements.

BACKGROUND OF THE INVENTION

Modern healthcare environments require systems capable of ingesting, processing, and acting upon diverse clinical data in real-time. Existing solutions are limited by mono-lingual interfaces, insufficient support for traceable device actuation, and a lack of regulatory compliance for autonomous AI actions. There remains a need for a comprehensive, multilingual healthcare system that delivers auditable clinical decision support, facilitates secure closed-loop device control, and adapts outputs to user roles, languages, and jurisdictional policies.

The disclosed system provides such technical improvements by (i) reducing end-to-end clinical-insight latency from ≥60 s to ≤5 s through hardware-accelerated parallel inference pipelines, (ii) enforcing cryptographically signed, role-based co-signature gates that materially improve cyber-security over prior art, and (iii) embedding a deterministic constraint-grammar checker that prevents malformed instructions from reaching therapy-delivery devices, thereby enhancing patient safety at a low-level machine interface.

SUMMARY OF THE INVENTION

The present invention provides a multilingual, AI-powered healthcare system configured to deliver real-time clinical insight, role-specific overlays, and traceable alert and control actions across a range of regulated environments. The system combines a personalized assistant engine, a classification model, multilingual rendering layers, and override-guarded actuation capabilities. By integrating signal ingestion, longitudinal state modelling, and language-specific interface layers, the invention bridges the gap between data collection, insight generation, and device-level execution. It supports multilingual output, role-specific interaction, co-signature enforcement, trace logging, and real-time safety controls necessary for use in regulated clinical workflows.

In one embodiment, the system is implemented as a non-transitory computer-readable medium storing processor-executable instructions that, when executed by one or more hardware processors (e.g., central processing units (CPUs), graphics processing units (GPUs), tensor processing units (TPUs)), perform the steps of:

(a) receiving heterogeneous clinical data streams via a secure interface conforming to the Health Level Seven® Fast Healthcare Interoperability Resources (HL7® FHIR) standard;

(b) updating a longitudinal patient state vector in shared memory. The Longitudinal Patient State is a time indexed vector representation that aggregates discrete and continuous patient data to provide historical context for AI inference;

(c) generating a triage score using a deep neural network trained on at least $10^7$ labelled patient-hour observations;

(d) invoking a large-language-model-powered assistant to (i) formulate a natural-language explanation of said triage score and (ii) output machine-readable clinical insights identifying at least one adjustable parameter of a connected medical device;

(e) translating the clinical insights into a device-control command packet that encodes said adjustable parameter;

(f) verifying proposed device-control commands with a deterministic constraint-grammar finite-state machine; and (g) dispatching signed commands to an external infusion pump over a mutually authenticated TLS 1.3 channel.

DETAILED DESCRIPTION OF THE PREFERRED EMBODIMENTS

The disclosed invention provides a comprehensive, multilingual healthcare insight system that integrates structured and unstructured clinical data to produce real-time patient understanding, role-specific interaction, and closed-loop control of connected medical devices. The system is configured to operate in regulated clinical environments, such as hospitals, ambulatory centres, and remote monitoring platforms, and supports patient- and provider-facing use cases simultaneously.

Figure 1:
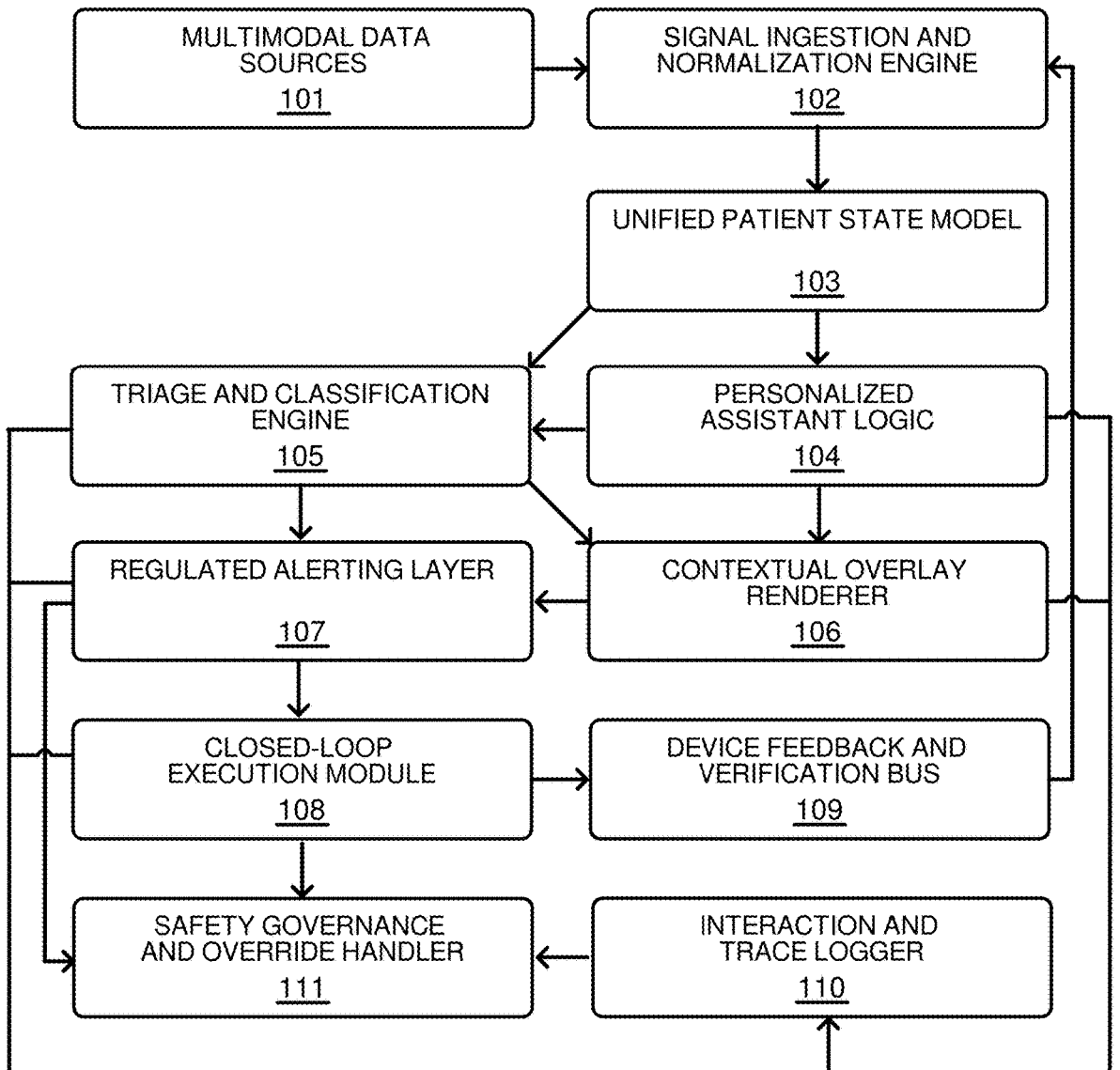
FIG. 1 is a high-level block diagram of the multilingual, AI-powered healthcare platform, showing the data-ingestion pipeline, longitudinal patient-state model, insight-generation components, regulated alerting layer, closed-loop device-control path, and safety-governance subsystems.

System Overview—Multilingual AI Powered Healthcare Framework:

As depicted in FIG. 1, multiple Multimodal Data Sources 101—for example, bedside monitors, wearables, electronic health-record (EHR) feeds, imaging devices, and voice-note repositories—stream raw signals to a Signal Ingestion and Normalization Engine 102. The engine 102 is designed to ingest, normalize, and interpret structured and unstructured clinical data—including physiological signals, metadata, EMR entries, wearable device streams, voice prompts, and manual user input—from a plurality of external sources via an interface conforming to an industry standard (for e.g. HL7® FHIR). The engine has high throughput data pipelines that receive raw physiological signals and transform them into standardized, timestamp aligned feature tensors. Engine 102 temporally aligns, de-duplicates, and unit-normalizes heterogeneous inputs before storing them in a Unified Patient State Model 103 that captures both instantaneous and longitudinal context. Unified Patient State Model 103 is a centralized data structure, persisted in an ACID (Atomicity, Consistency, Isolation, Durability) compliant database, that stores the latest Longitudinal Patient State for reference by all system modules. A Personalized Assistant Logic module 104 consumes the evolving longitudinal patient state vector and, in cooperation with the Triage and Classification Engine 105, produces role-tailored insights, acuity labels, and next-best-action recommendations. The Triage and Classification Engine 105 is a deep learning model ensemble that fuses physiological data, historical trends, and contextual modifiers to generate real time acuity labels. These outputs are rendered by the Contextual Overlay Renderer 106, which in turn furnishes visual, audio, or avatar surfaces across clinician dashboards and patient-facing devices. Parallel to rendering, a Regulated Alerting Layer 107 determines if any insight satisfies jurisdiction-specific escalation criteria. Qualified events propagate to downstream secure-messaging or paging channels while being queued for approval by the Closed-Loop Execution Module 108 when device actuation is involved. The module 108 interfaces with a Device Feedback and Verification Bus 109 to confirm receipt of the device's command, monitor device telemetry, and detect execution anomalies.

All conversational turns, model inferences, alerts, and actuator commands are persisted by an Interaction and Trace Logger 110, feeding audit-readiness and model-explainability tooling. Finally, a Safety Governance and Override Handler 111 enforces co-signature, credential gating, and policy rollback, ensuring that any autonomous path can be halted or reversed in real-time.

The system generates a longitudinal patient-state model, enabling context-aware, real-time clinical reasoning and traceable device actuation.

Hardware Environment. Each computing node 120 (not shown) includes: (i) at least one multi-core CPU; (ii) a GPU or TPU accelerator; (iii) 32 GB-2 TB of volatile memory; (iv) a secure element storing cryptographic keys; and (v) a network interface controller supporting IEEE 802.1AE MACsec (MACsec (Media-Access-Control Security) encryption. Nodes communicate over a redundant 100 GbE spine-leaf fabric within a hospital private cloud.

Figure 2:
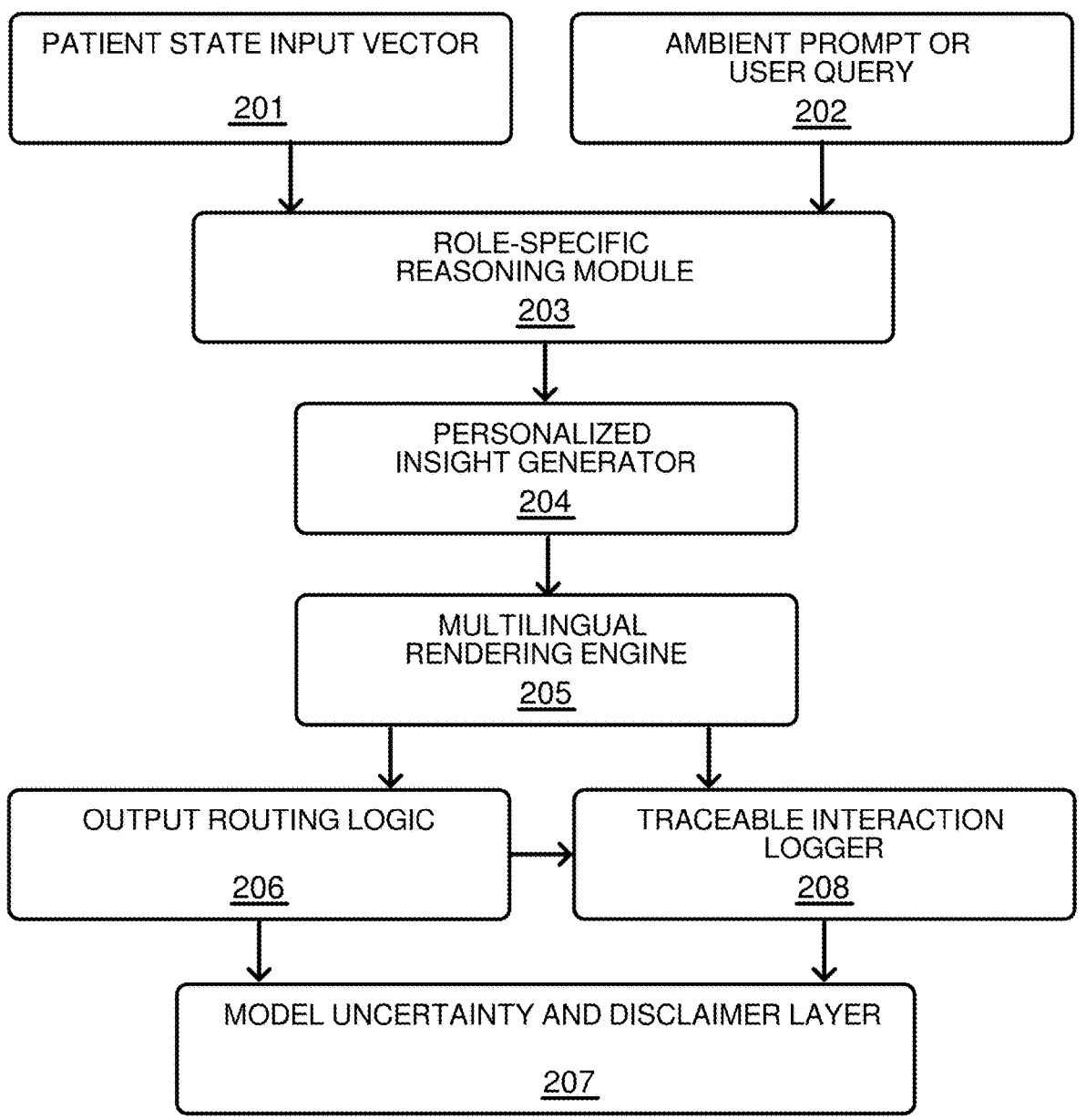
FIG. 2 is a functional block diagram of the Personalized Medical-Assistant Engine, detailing how patient-state vectors and user prompts are processed through role-specific reasoning, multilingual rendering, uncertainty tagging, and trace logging.

Personalized Medical Assistant Engine:

As illustrated in FIG. 2, the Personalized Medical-Assistant Engine is instantiated as a privacy-preserving large-language-model stack that has been (i) pretrained on a two-trillion-token multilingual corpus spanning more than 200 languages and (ii) fine-tuned on a six-million-document clinical dataset (MIMIC-IV Global) under a differential-privacy budget of $\varepsilon<5$, thereby satisfying HIPAA Safe-Harbor de-identification requirements. During a subsequent policy-alignment phase the model is reinforced to comply with jurisdiction-specific disclosure rules, scope-of-practice constraints, and institutional style guides, ensuring that every downstream utterance remains within authorised clinical boundaries while retaining terminological fidelity (ICD-10, SNOMED, LOINC). The resulting inference core is deployed as a containerised micro-service that exposes gRPC (Google Remote Procedure Call) and FHIR-compatible endpoints for low-latency integration with electronic-medical-record systems, bedside middleware, and wearable-sensor gateways.

At run time—and again with reference to FIG. 2—a temporally aligned Patient-State Input Vector 201 (vitals, labs, medication-adherence flags, imaging tags, contextual risk scores) and an Ambient Prompt or User Query 202 are fed into a Role-Specific Reasoning Module 203 that constrains vocabulary, disclosure depth, and recommended actions to the privileges of an authenticated user. A Personalized Insight Generator 204 then emits structured triage labels, differential considerations, and next-best-action recommendations, which the Multilingual Rendering Engine 205 localises into more than eighty languages with automatic handling of reading direction, register, and health-literacy level. Delivery is orchestrated by Output Routing Logic 206, selecting one or more surfaces—heads-up multilingual overlay, EHR note, secure message, voice call, or AR visor—while a Model-Uncertainty & Disclaimer Layer 207 decorates low-confidence passages with uncertainty brackets or jurisdiction-mandated disclaimers. Every prompt, token output, confidence metric, routing decision, and localisation artefact is committed by the Traceable Interaction Logger 208 to an immutable, tamper-evident ledger, thereby providing end-to-end auditability in accordance with 21 CFR Part 11 and EU MDR record-keeping standards.

Figure 5:
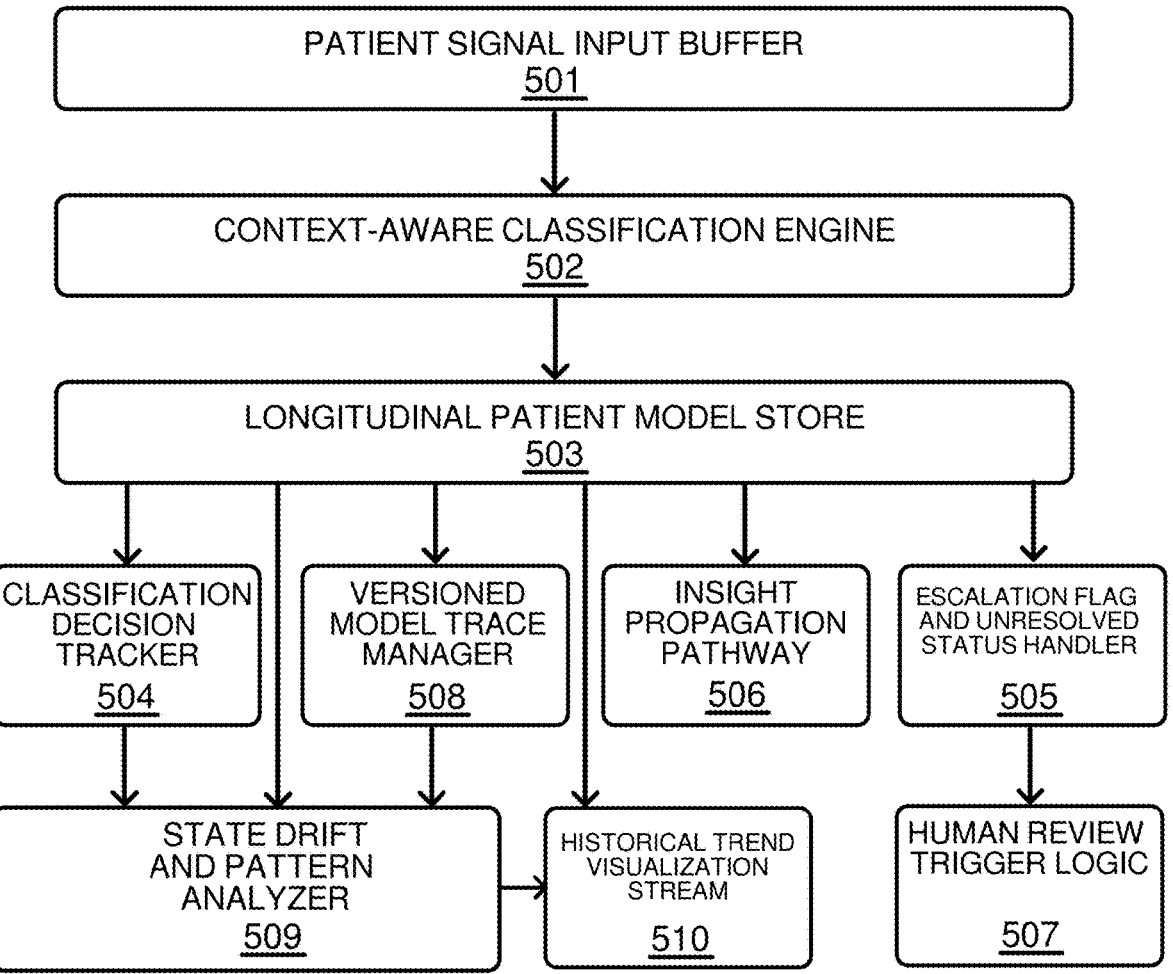
FIG. 5 is a block diagram of the asynchronous patient-classification engine, showing real-time signal buffering, context-aware classification, longitudinal model storage, escalation logic, drift analysis, and historical-trend visualization.

Multilingual Triage and Classification Engine:

The Multilingual Triage and Classification Engine continuously fuses streaming physiological telemetry with the patient's prior state trajectory and situational context to produce up-to-the-second acuity labels and decision-support primitives. As depicted in FIG. 5, the complete set of structured telemetry—including physiologic waveforms, laboratory deltas, medication-adherence ticks, and environmental metadata—first accumulates in Patient-Signal Input Buffer 501, where each record is time-aligned and sanity-checked for out-of-range values or missing data. These harmonised signals feed directly into a Context-Aware Classification Engine 502, which executes a hybrid of gradient-boosted decision trees and transformer attention layers to infer moment-to-moment triage states such as "stable," "watch," or "critical." The resulting labels, probability vectors, and explanatory feature weights are then persisted in a Longitudinal Patient Model Store 503, creating a continuously expandable timeline that subsequent modules can interrogate.

Each new inference simultaneously activates multiple parallel post-processing branches. First, a Classification-Decision Tracker 504 records the model version, input-data hashes, and latency metrics. In parallel, an Escalation Flag & Unresolved-Status Handler 505 inspects the result for threshold breaches, missing confirmations, or conflicting trends. Thereafter, a Human-Review Trigger Logic 507 independently queues borderline or low-confidence cases for synchronous specialist validation. Concurrent to 504 and 505, an Insight-Propagation Pathway 506 forwards the freshly computed acuity label to downstream subsystems—such as the Contextual Overlay Renderer 106 and the Regulated Alerting Layer 107—so that visual dashboards and alert channels reflect the latest patient state.

To guarantee scientific reproducibility, a Versioned-Model Trace Manager 508 snapshots the active classifier weights and hyper-parameters each time the engine is updated, thereby allowing forensic re-execution of any past decision. In parallel, a State Drift and Pattern Analyzer 509 scans the longitudinal store for subtle trajectory shifts—such as gradually deteriorating renal function or cyclic heart-rate variability—that may not trip instantaneous thresholds; the output from analyzer 509 feeds a Historical-Trend Visualization Stream 510, which surfaces interactive sparklines and deviation heat-maps to remote intensivists and quality-improvement teams.

Operating in concert with the Personalized Medical-Assistant Engine described earlier, this classification subsystem delivers normalised, language-agnostic acuity signals to all downstream renderers and actuation modules, thereby ensuring that every overlay, alert, and closed-loop device command is anchored to a rigorously audited understanding of the patient's evolving physiological state.

Figure 3:
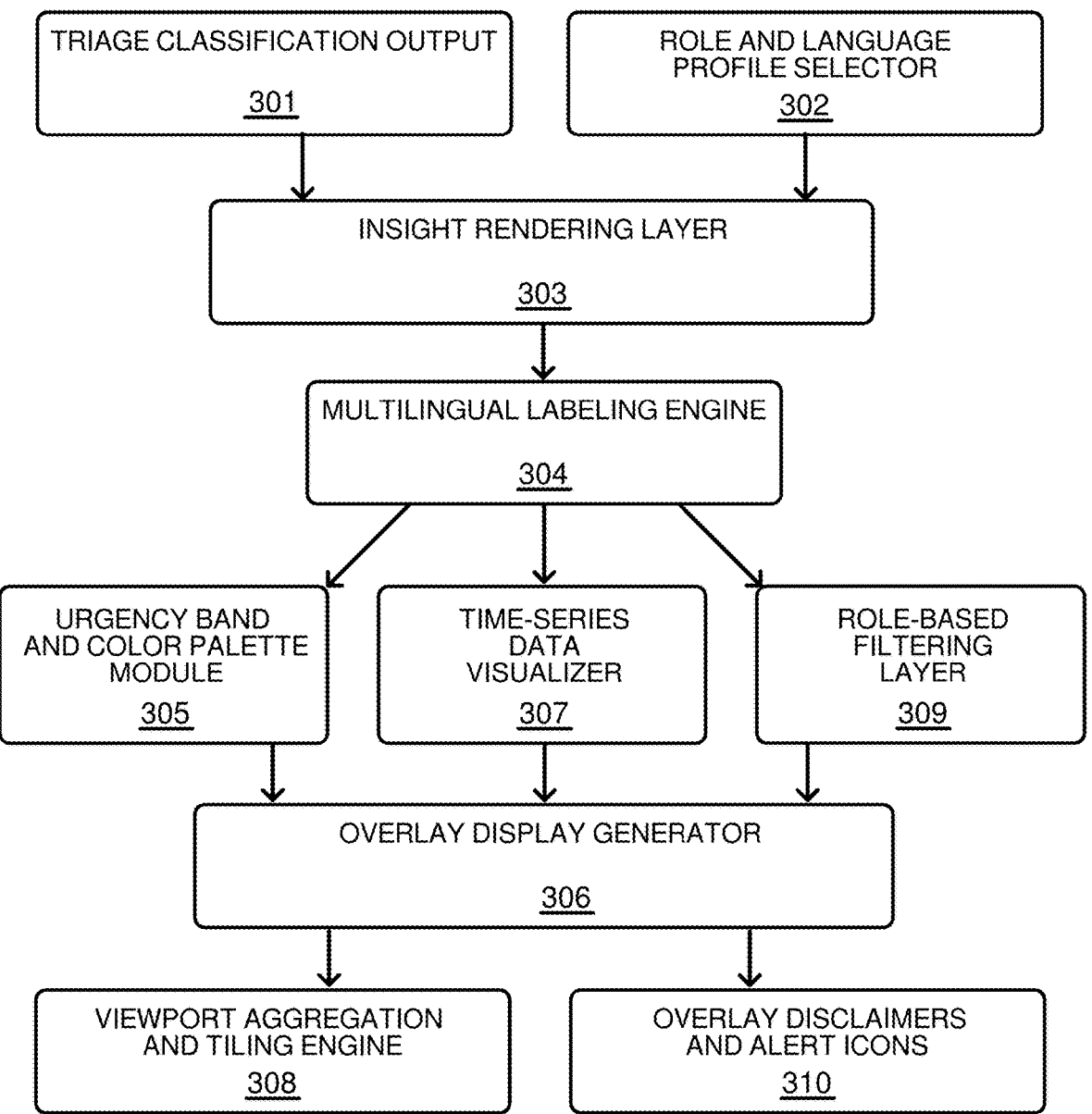
FIG. 3 is a schematic of the contextual overlay-generation subsystem, illustrating how triage outputs are transformed—via role and language selection, urgency-banding, and visual-layer composition—into culturally adaptive dashboards and avatar surfaces.

Contextual Overlay-Generation Subsystem:

As schematically depicted in FIG. 3, the contextual overlay-generation subsystem, or Multilingual Overlay Renderer, converts raw triage findings into linguistically and culturally adaptive information overlays and insights that can be projected on wall monitors, tablets, wrist-watches, or avatar surfaces. Operation begins when a Triage Classification Output 301—generated upstream by the classification engine—enters a Role-and-Language Profile Selector 302 that references both the authenticated viewer's access privileges and their preferred locale. The selector injects role-appropriate tone (e.g., plain-language for a family member versus ICD-10 terminologies for a physician) and chooses the correct reading direction, numeric separators, and date formats.

The localized narrative first moves through Insight Rendering Layer 303, where prose, charts, and actionable bullet points are laid out. Immediately downstream, a Multilingual Labeling Engine 304 replaces every axis title, tick label, and call-out with correctly gendered, inflected, and alphabet-aligned equivalents across more than eighty languages.

From that point three sub-processes operate in parallel:

an Urgency-Band & Color-Palette Module 305 maps the current acuity score to an institution-approved hue gradient (e.g., green→amber→red) and adds pattern overlays for colour-blind accessibility;

a Time-Series Data Visualizer 307 streams numeric trend lines, sparklines, or radar plots that contextualise the narrative; and a Role-Based Filtering Layer 309 removes restricted attributes—such as mental-health codes or genetic findings—whenever the viewer lacks the requisite clearance, thereby enforcing least-privilege disclosure in real time.

The outputs of Modules 305, 307, and 309 converge in an Overlay Display Generator 306, which composes a single, harmonised scene and automatically balances font sizes and aspect ratios so that the same insight appears coherent on a 55-inch nurse-station panel or a 1.9-inch smartwatch.

Finally, the composite scene fans out to two parallel post-processors: a Viewport Aggregation & Tiling Engine 308, which prioritises widgets when screen real estate is constrained, and an Overlay Disclaimers & Alert-Icon Layer 310, which appends jurisdiction-specific footers ("AI-generated clinical decision support—verify before acting") and inserts modality-specific icons (e.g., fall-risk, isolation, radiation caution) so that frontline staff can recognise critical status at a glance.

Beyond flat graphics, the same rendering pipeline includes an avatar-based communication interface that (i) converts each localised narrative into synchronised speech synthesis aligned at the viseme level, (ii) dynamically modulates voice pitch, cadence, and volume to match the inferred urgency of the underlying triage state, and (iii) animates facial expressions and gesture sets drawn from a culturally adaptive motion library. By coordinating lip-sync, prosody, and body language, the interface presents a virtual caregiver whose tone and non-verbal cues reinforce comprehension and empathy—whether the viewer is a paediatric patient using a tablet, a family member on a smartphone, or a clinician wearing mixed-reality glasses. This avatar channel allows complex or sensitive findings—such as a new cancer diagnosis—to be delivered with empathetic tone and regulated disclosures in the patient's preferred language. All overlays, whether graphical or avatar, may be simultaneously exported to a secure, caregiver-accessible dashboard that honours the same role and language filters, enabling remote monitoring while preserving privacy and auditability. In this fashion the system ensures that every stakeholder receives an instantly comprehensible, appropriately scoped, and fully traceable view of the patient's state, irrespective of language, literacy, or device constraints.

Figure 4:
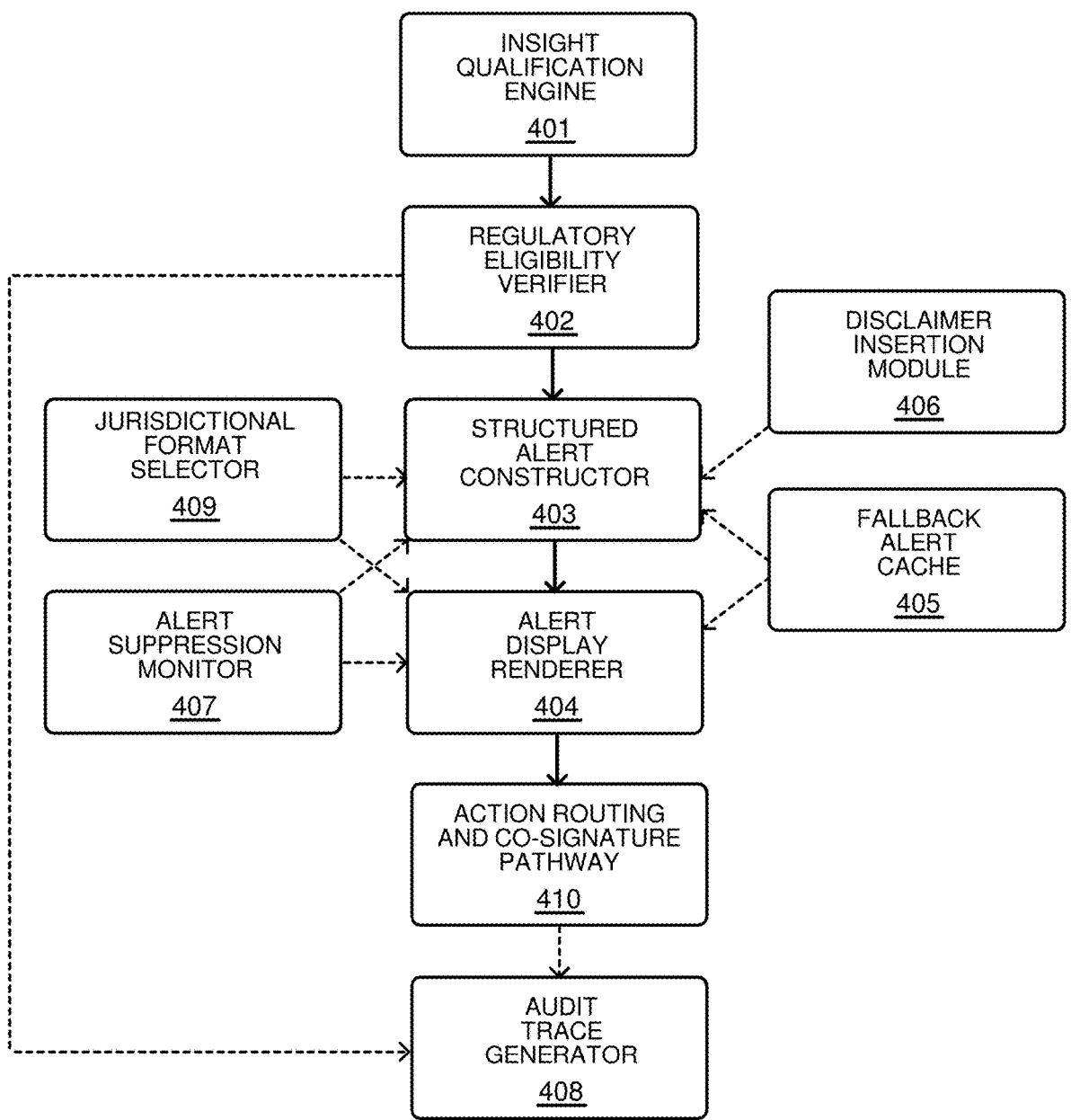
FIG. 4 is a flow diagram of the regulated alerting subsystem, depicting insight qualification, jurisdictional eligibility checks, alert construction, disclaimer insertion, suppression logic, audit-trace generation, and co-signature routing.

Regulated Alerting and Traceable Insight Layer:

FIG. 4 presents the workflow of the policy-aware alerting service that transforms raw clinical insights into regulatorily compliant, fully auditable notifications. Processing commences when an insight arrives at the Insight Qualification Engine 401, which tests the clinical relevance and compares urgency thresholds against institution-defined escalation matrices. Only if the finding is deemed actionable does it proceed to a Regulatory Eligibility Verifier 402, where machine-readable policy tables for HIPAA, GDPR, EU MDR, and other regional statutes are consulted; data elements disallowed by a given jurisdiction are redacted or abstracted at this stage, ensuring downstream payloads never exceed authorised disclosure bounds.

After the insight clears the Regulatory-Eligibility Verifier 402—or is suppressed therein for non-compliance—the event is immediately recorded by the Audit-Trace Generator 408, ensuring that every pass or fail is immutably logged.

For insights that are approved, a Jurisdictional Format Selector 409 first determines the statutory output template (HL7 v2, FHIR R4, CDA L3, or a region-mandated PDF) and passes that formatting guidance in parallel to both the Structured-Alert Constructor 403 and the Alert-Display Renderer 404.

Fallback Alert Cache 405 stores a library of plain-text, low-bandwidth templates. Whenever an alert is being built, both the Structured-Alert Constructor 403 and the Alert-Display Renderer 404 pull the appropriate cached template, merge it with the current machine-parsable codes and human-readable narrative, and then format the result according to the jurisdictional schema dictated by Selector 409. Constructor 403 serialises the completed payload into the canonical machine schema, while Renderer 404 generates a live rich-media preview for the originator; if the recipient device cannot render rich media, the very same fallback text from Cache 405 is served instead.

Before the preview is finalised, a Disclaimer Insertion Module 406 appends region-specific legal boiler-plate ("AI-assisted clinical decision support—verify before acting," localised as required) and annotates machine recommendations with confidence bands. A concurrent Alert-Suppression Monitor 407 cross-checks recent notifications and paging windows, throttling redundant or non-urgent duplicates to combat alert fatigue.

The fully rendered alert then flows from Renderer 404 into an Action-Routing & Co-Signature Pathway 410, which consults role hierarchies, shift rosters, and MFA policies to decide whether single-click acknowledgement suffices or whether dual sign-off is mandatory (e.g., narcotic dosage changes). If co-signature is required, Pathway 410 queues the alert in a time-bounded adjudication pool; failure to obtain timely approval escalates to the next on-call credential group.

All disposition codes—delivered, escalated, suppressed, or expired—are fed back to the Audit-Trace Generator 408, completing a verifiable, closed-loop chronology of the alert's lifecycle.

Figure 6:
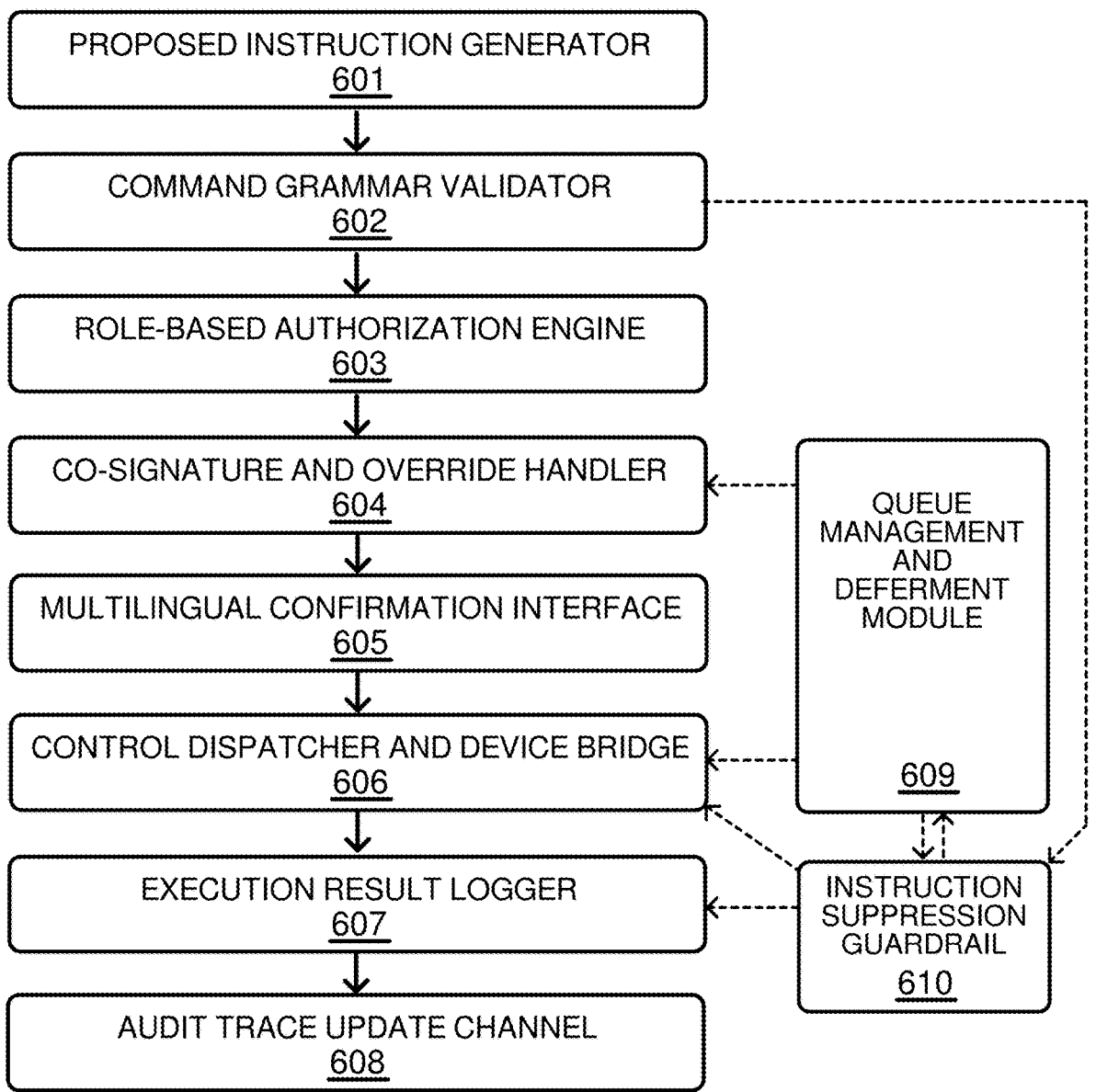
FIG. 6 is a pipeline diagram of the closed-loop device-control workflow, highlighting instruction generation, grammar validation, role-based authorization, multilingual confirmation, device bridging, execution logging, and safety guardrails.

Device Control and Override Execution Layer:

FIG. 6 traces the full closed-loop workflow that turns a validated clinical insight into a cryptographically signed, policy-bounded command for a connected medical device. The sequence begins inside a Proposed Instruction Generator 601, which formulates a machine-readable control packet—e.g., "reduce infusion rate by 0.4 mL h⁻¹"—together with metadata describing the originating insight, the patient identifier, and the required quality-of-service window. Immediately thereafter the packet's syntax, units, and device-library compatibility are scrutinised by a Command-Grammar Validator 602; malformed verbs, off-label drug names, and out-of-range numeric fields are rejected before any network transmission is attempted.

Once grammatical integrity is confirmed, the command is routed to a Role-Based Authorization Engine 603 that consults institutional policy tables and active-directory tokens to verify that the requester possesses the minimum credential tier for the specified device class. If the action is categorised as "high risk"—for example, titrating vasoactive drips or altering ventilator pressures—the flow automatically enters a Co-Signature and Override Handler 604. This dual-control subsystem requires a second credential holder to affix a FIPS 140-3-compliant digital signature, generated and stored inside a hardware-security module, before execution can proceed. The pending request is displayed on bilingual confirmation screens rendered by the Multilingual Confirmation Interface 605, ensuring that each approver sees the same instruction in their preferred language together with unambiguous dosage units and patient context.

Following successful authorisation, a Control Dispatcher and Device Bridge 606 serialises the packet (Protocol Buffers v3), hashes it with SHA-3-256, and signs it using an ECDSA-P-384 private key resident in the HSM. Encapsulated in gRPC over TLS 1.3, the packet is then delivered to the target device; in one preferred embodiment the bridge integrates with a Baxter Spectrum IQ infusion pump, which responds with an execution acknowledgement within approximately 50 milliseconds. The round-trip payload, the device's ACK/NACK code, and any telemetry echo are captured by an Execution-Result Logger 607, while an Audit-Trace Update Channel 608 commits a cryptographic digest of the entire transaction—proposal, approvals, dispatch time-stamps, and device receipt—to the system's tamper-evident ledger.

To guard against burst traffic or transient network faults, the pipeline includes a Queue-Management and Deferment Module 609 that rate-limits successive instructions and automatically reschedules those that miss their QoS window. In parallel, an Instruction-Suppression Guardrail 610 cross-checks the live drug library, device status, and patient-allergy list; any mismatch or post-dispatch device alarm triggers an immediate rollback command and raises an escalated alert. Throughout the process a secure message center—an end-to-end-encrypted communication bus with automatic language translation and role-based visibility—mirrors status updates to all relevant clinicians, embedding cryptographically verifiable links back to the ledger so that every approval, rejection, or rollback is fully auditable. The bus is realised as an Apache Kafka® message topic with TLS 1.3 transport and OAuth 2.0 client credentials. Only when each of these safeguards has been satisfied does the system regard the control cycle as closed, thereby aligning rapid bedside automation with stringent safety, privacy, and regulatory mandates.

Infrastructure Integration and Signal Governance:

The system integrates with third-party EMRs, wearable sensors, hospital middleware, and cloud-based health-data services via a pluggable device-integration layer and normalized protocols. The pluggable device-integration Layer is a driver framework that exposes uniform gRPC or RESTful interfaces for heterogeneous medical devices using vendor specific protocol adapters. The integration layer manages secure data ingestion, normalization, synchronization, and orchestration.

All patient data transmissions within the system, and between integrated third-party platforms, are encrypted using standards-based protocols to ensure confidentiality and regulatory compliance.

The system further comprises a medication adherence module configured to monitor, analyze, and detect anomalies in scheduled medication intake. The module is a subsystem that correlates smart-dispenser logs, eMAR entries, and patient self-reports to detect missed or delayed doses.

The module integrates with smart dispensers and electronic Medication Administration Record (eMAR) systems to retrieve real-time and historical medication administration data. The smart dispenser is an electronically controlled medication dispenser that logs dose release times and communicates over Bluetooth® Low Energy (BLE), Wi-Fi 6, or Zigbee® to the Medication Adherence Module. eMAR (electronic Medication Administration Record) represents a digital record system that logs medication administrations, dosage, and timing, replacing paper MARs and enabling automated adherence analytics. By comparing scheduled dosing events with actual administration times and methods, the module detects deviations, omissions, or delays and generates traceable alerts or summaries for care providers. Detected anomalies are flagged for clinical review and may be rendered via multilingual overlays or secure message channels, ensuring timely intervention and improving patient safety. A "Write-Once, Read-Many" (WORM) object store provides immutable retention of medication-adherence logs for regulatory audits.

Deployment Modes and Safety Architecture:

The architecture supports cloud-based, hybrid edge-cloud, and offline deployment, ensuring adaptability to hospital, ambulatory, and remote-care settings. Safety features include redundancy, secure access controls, and multi-factor overrides for critical actions.

Example Use Case:

A patient's wearable sensor reports a critical physiological parameter. The signal is ingested, modeled longitudinally, and triggers the Assistant Engine to generate a multilingual summary and a regulated alert for the attending nurse. The alert is rendered as a color-coded overlay and delivered via secure message and avatar interface. After co-signature from the provider, a closed-loop device command is issued to adjust therapy, with all steps logged in an immutable audit record, i.e., a blockchain-backed or WORM (Write-Once, Read-Many) storage ledger that ensures post facto integrity and non-repudiation of system actions.

Figure 7:
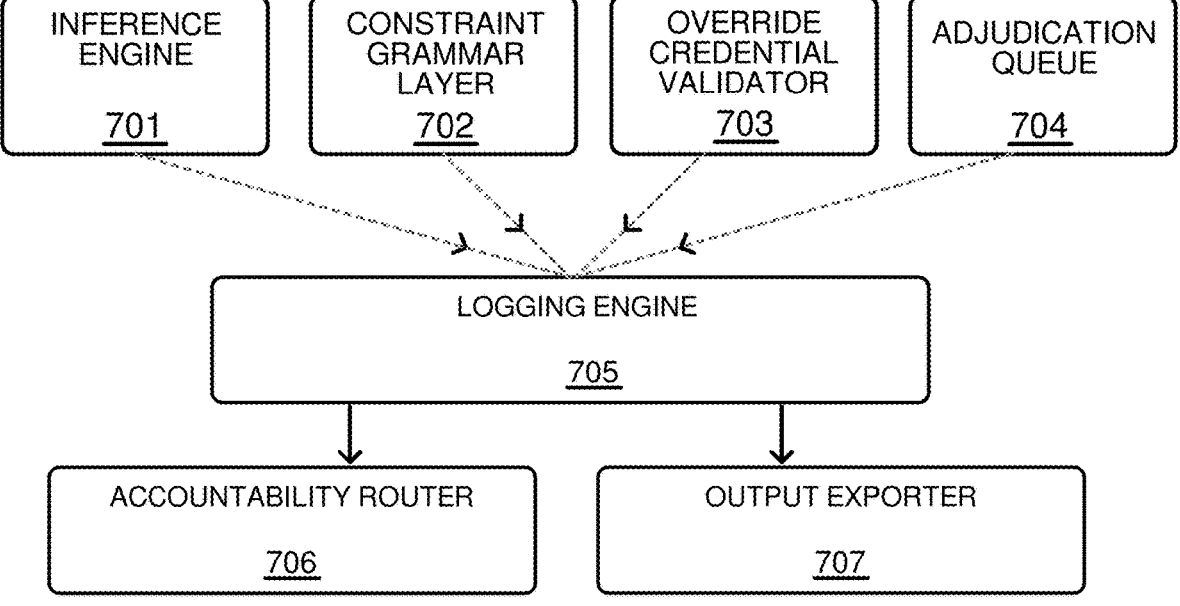
FIG. 7 is an architectural diagram of the security, explainability, and compliance framework, illustrating the inference engine, constraint-grammar layer, override-credential validator, adjudication queue, immutable logging engine, accountability router, and output exporter.

Agentic AI Architecture:

As shown in FIG. 7, the system's governance layer is anchored by an Inference Engine 701 that continuously synthesises candidate clinical actions from the longitudinal patient model, the current device state, and institutional policy graphs. Each proposal is immediately screened by a Constraint-Grammar Layer 702—a deterministic finite-state machine that enforces both syntactic correctness (e.g., dosage units, verb tense, device-library tokens) and semantic legality (scope-of-practice limits, formulary restrictions, jurisdictional disclosure caps). Proposals that satisfy grammar constraints are then subjected to credential scrutiny by an Override-Credential Validator 703, which verifies multi-factor tokens, checks active-directory group memberships, and compares the requested action against any standing override or lockout rules.

If a command still passes muster, it enters an Adjudication Queue 704, implemented as a persistent, cryptographically tagged message topic (e.g., Apache Kafka®) that guarantees at-least-once delivery and allows asynchronous human sign-off. High-priority items bubble to the top of the queue, while low-risk suggestions may auto-expire if superseded by fresher telemetry. Regardless of outcome—approval, modification, or rejection—every step is timestamped and chained by a Logging Engine 705 to a tamper-evident ledger, creating an immutable explainability trace that satisfies 21 CFR Part 11, EU MDR, and the emerging EU AI Act transparency mandates.

Once adjudication is complete, an Accountability Router 706 chooses the dissemination path: provider dashboards for immediate bedside action, FHIR notes for electronic-health-record continuity, regulatory APIs for mandated reporting, or secure overlays for family notification. A downstream Output Exporter 707 then bundles the final decision, together with reference hashes of all contributing data and model artefacts, into digitally signed evidence packages suitable for external auditors, post-market surveillance bodies, or machine-learning retraining pipelines. In this way, the agentic AI layer guarantees that every autonomous—or semi-autonomous—recommendation travels through a rigorously policed gauntlet of policy checks, credential validation, human review, and cryptographic logging before it can affect patient care or device behaviour, thereby unifying safety, explainability, and regulatory compliance in a single architectural tier.

The claimed subject matter is directed to a specific, technological improvement in the functioning of computer networks and medical devices. The invention is not merely a mental process nor an abstract idea implemented on a generic computer. Rather, it recites (i) specialized data-normalization circuits, (ii) deterministic constraint-grammar modules that transform logically structured commands into low-level actuation signals, and (iii) role-based cryptographic co-signature pathways that materially improve the cybersecurity and safety of network-connected infusion pumps.

While the present disclosure has been described with reference to exemplary embodiments, those skilled in the art will recognize that modifications may be made without departing from the scope of the claimed invention.

What is claimed is:

1. A multilingual, AI-powered healthcare system comprising:

a signal-ingestion engine for receiving heterogeneous clinical-data streams over a standards-based interface and generating time-aligned, unit-normalized feature tensors;

a longitudinal patient-state store that persistently maintains an instantaneous and historical vector representation of each patient;

a triage and classification engine operatively coupled to the patient-state store and trained on at least ten million ($10^7$) labelled patient-hour observations, the engine outputting a current acuity label for the patient;

a personalized medical-assistant engine that includes a large-language-model core and generates a natural-language explanation of the acuity label and machine-readable clinical insights identifying at least one adjustable parameter of a connected medical device;

a contextual overlay renderer transforming the clinical insights into role-specific, multilingual information overlays for display on one or more user devices;

a regulated alerting subsystem evaluating each clinical insight against jurisdiction-specific rules, constructing an alert in a canonical schema, and routing the alert for single or dual sign-off;

a device-control and override-execution module, the module performing the functions of translating the clinical insights into a device-control command packet, verifying the packet with a deterministic constraint-grammar finite-state machine, applying role-based authorization with optional dual cryptographic co-signature, and dispatching a signed command to the connected medical device over a mutually authenticated TLS 1.3 channel; and, an immutable audit ledger that records, in tamper-evident form, every acuity label, alert lifecycle event, authorization decision, and device-command transaction generated by the triage and classification engine, the personalized medical-assistant engine, the contextual overlay renderer, the regulated alerting subsystem, and the device-control and override-execution module.

2. The system of claim 1, wherein the signal-ingestion engine conforms to HL7® FHIR standards and automatically de-duplicates incoming messages.

3. The system of claim 1, wherein the personalized medical-assistant engine is pretrained on a multilingual corpus of at least two trillion tokens and fine-tuned on a six-million-document clinical dataset under a differential-privacy budget $\varepsilon < 5$.

4. The system of claim 1, wherein the contextual overlay renderer includes a role-based filtering layer that suppresses restricted data elements for unauthorized viewers.

5. The system of claim 1, wherein the regulated alerting subsystem includes a fallback alert cache storing plain-text templates that are automatically substituted on low-bandwidth endpoints.

6. The system of claim 1, wherein the deterministic constraint-grammar finite-state machine rejects device-control packets containing out-of-range dosage values or unrecognized drug identifiers.

7. The system of claim 1, wherein the device-control and override-execution module requires a FIPS 140-3-compliant dual digital signature for any command involving vasoactive medication.

8. The system of claim 1, wherein the audit ledger is implemented as a write-once, read-many (WORM) object store or blockchain ledger that provides post-facto integrity and non-repudiation.

9. The system of claim 1, further comprising a secure message center realized as an Apache Kafka® topic protected by TLS 1.3 transport and OAuth 2.0 client credentials.

10. The system of claim 1, wherein the multilingual information overlay further comprises an avatar-based communication interface generating synchronized speech synthesis and culturally adaptive gestures.

11. The system of claim 1, further comprising a medication adherence module detecting anomalies in scheduled medication intake via smart dispensers or eMAR logs.

12. A computer-implemented method for multilingual, AI-assisted clinical decision support and closed-loop device control, the method comprising:

(a) receiving heterogeneous clinical-data streams via a standards-based interface and converting the received data into time-aligned, unit-normalized feature tensors;

(b) updating a longitudinal patient-state vector of a patient in shared memory with the feature tensors;

(c) generating a current acuity label for the patient by applying a deep-learning triage and classification model trained on at least ten million ($10^7$) labelled patient-hour observations to the longitudinal patient-state vector;

(d) producing, with a large-language-model-based assistant (i) a natural-language explanation of the acuity label, and (ii) machine-readable clinical insights that identify at least one adjustable parameter of a connected medical device;

(e) rendering the clinical insights as role-specific, multilingual information overlays on one or more user devices;

(f) evaluating the clinical insights against jurisdiction-specific alert rules for constructing a structured alert in a canonical schema and routing the alert for single or dual sign-off;

(g) translating the clinical insights into a device-control command packet;

(h) verifying the device-control command packet with a deterministic constraint-grammar finite-state machine;

(i) authorising the verified command packet via role-based authentication that optionally requires a dual cryptographic co-signature;

(j) dispatching the authorised, cryptographically signed command packet to the connected medical device over a mutually authenticated TLS 1.3 channel; and (k) recording, in an immutable audit ledger, each acuity label, alert lifecycle event, authorisation decision, and device-command transaction created during steps (c) through (j).

13. The method of claim 12, wherein the standards-based interface conforms to the HL7® FHIR specification and automatically de-duplicates redundant messages.

14. The method of claim 12, wherein the large-language-model-based assistant is pretrained on a multilingual corpus of at least two trillion tokens and fine-tuned on a six-million-document clinical dataset under a differential-privacy budget $\varepsilon < 5$.

15. The method of claim 12 further comprises filtering restricted data elements from the information overlays when a viewer's access privileges do not permit disclosure of those elements.

16. The method of claim 12 further comprises storing a plain-text fallback version of the structured alert in a cache and automatically substituting the fallback alert when the recipient device lacks rich-media capability or is operating over a low-bandwidth connection.

17. The method of claim 12, wherein the verifying the device-control command packet comprises rejecting any device-control command packet that contains an out-of-range dosage value or an unrecognised drug identifier.

18. The method of claim 12, wherein the authorising the verified command packet requires a FIPS 140-3-compliant dual digital signature for any command packet that adjusts a vasoactive medication parameter.

19. The method of claim 12, wherein the recording in an immutable audit ledger comprises storing each entry in a write-once, read-many (WORM) object store or blockchain ledger to ensure post-facto integrity and non-repudiation.

20. The method of claim 12 further comprising streaming the natural-language explanation and the acuity label to a secure message centre implemented as an Apache Kafka® topic protected by TLS 1.3 transport and OAuth 2.0 client credentials.

21. The method of claim 12, wherein the rendering the clinical insights further comprises generating, via an avatar-based communication interface, synchronised speech synthesis and culturally adaptive gestures corresponding to the information overlays.

22. The method of claim 12 further comprising detecting, with a medication-adherence module, anomalies in scheduled medication intake by correlating smart-dispenser logs with electronic medication-administration-record entries and, upon detecting an anomaly, triggering the evaluation of clinical insights to generate an alert for clinical review.

* * * * *